US012655110B2

(12) United States Patent
Buschmann et al.

(10) Patent No.: US 12,655,110 B2
(45) Date of Patent: Jun. 16, 2026

(54) METHOD OF PRODUCING A CRYSTALLINE FORM OF SODIUM 2-[(4S)-8-FLUORO-2-[4-(3-METHOXYPHENYL)PIPERAZIN-1-YL]-3-[2-METHOXY-5-(TRIFLUOROMETHYL) PHENYL]-4H-QUINAZOLINE-4-YL]ACETATE TRIHYDRATE

(71) Applicant: A1C246 AG & CO. KG, Wuppertal (DE)

(72) Inventors: Helmut Buschmann, Aachen (DE); Thomas Goldner, Velbert (DE); Jordi Carles Ceron Bertran, La Pobla de Montornes (ES)

(73) Assignee: AIC246 AG & CO. KG, Wuppertal (DE)

( * ) Notice: Subject to any disclaimer, the term of this patent is extended or adjusted under 35 U.S.C. 154(b) by 687 days.

(21) Appl. No.: 17/802,792

(22) PCT Filed: Mar. 1, 2021

(86) PCT No.: PCT/EP2021/055045

§ 371 (c)(1),
(2) Date: Aug. 26, 2022

(87) PCT Pub. No.: WO2021/170874

PCT Pub. Date: Sep. 2, 2021

(65) Prior Publication Data

US 2023/0219899 A1 Jul. 13, 2023

(30) Foreign Application Priority Data

Feb. 27, 2020 (EP) .................................... 20159727

(51) Int. Cl.

| | |
|---|---|
| ***C07D 239/84*** | (2006.01) |
| ***A61K 31/517*** | (2006.01) |
| ***A61P 31/22*** | (2006.01) |

(52) U.S. Cl.
CPC ........ *C07D 239/84* (2013.01); *C07B 2200/13* (2013.01)

(58) Field of Classification Search
CPC ...... C07D 239/84; A61K 31/517; A61P 31/22
See application file for complete search history.

(56) References Cited

U.S. PATENT DOCUMENTS

| | | | |
|---|---|---|---|
| 8,513,255 | B2 | 8/2013 | Wunberg et al. |
| 9,637,459 | B2 | 5/2017 | Grunenberg et al. |
| 2013/0066073 | A1 | 3/2013 | Goossen et al. |

FOREIGN PATENT DOCUMENTS

| | | | |
|---|---|---|---|
| WO | 2004096778 | A1 | 11/2004 |
| WO | 2006133822 | A1 | 12/2006 |
| WO | 2013127971 | A1 | 9/2013 |
| WO | 2021170875 | A1 | 9/2021 |
| WO | 2021170878 | A1 | 9/2021 |
| WO | 2021170879 | A1 | 9/2021 |
| WO | 2021170882 | A1 | 9/2021 |

OTHER PUBLICATIONS

European Search Report in corresponding EP20159727 Jun. 18, 2020 (pp. 1-6).
International Search Report PCT/EP2021/055045 dated Apr. 20, 2021 (pp. 1-3).
Brittain Harry G., "Methods for the Characterization of Polymorphs", 1999, pp. 235-238.
Caira Mino R. et al.: "Crystalline Polymorphism of Organic Compounds", Design of Organic Solids, Topics in Current Chemistry, Springer, Berlin, Heidelberg, 1998, vol. 198, pp. 163-208.

*Primary Examiner* — Bruck Kifle
(74) *Attorney, Agent, or Firm* — Millen, White, Zelano & Branigan, P.C.; Brion P. Heaney

(57) ABSTRACT

The present invention refers to an effective method of preparing a crystalline form of 2-[(4S)-8-fluoro-2-[4-(3-methoxyphenyl)piperazin-1-yl]-3-[2-methoxy-5-(trifluoromethyl) phenyl]-4H-quinazolin-4-yl]acetic acid sodium trihydrate.

29 Claims, 6 Drawing Sheets

Letermovir sodium methanol monohydrate

| | | |
|---|---|---|
| Space group: *R3* Trigonal | a = 28.0775 Å | α = 90 ° |
| Volume: 6866.2 $Å^3$ | b = 28.0775 Å | β = 90 ° |
| Density: 1.403 $g/cm^3$ | c = 10.0570 Å | γ = 120 ° |

Letermovir sodium ethanol monohydrate

| | | |
|---|---|---|
| Crystal system | Trigonal | |
| Space group | *R*3 | |
| Unit cell dimensions | a = 28.4046(16) Å | α = 90° |
| | b = 28.4046(16) Å | β = 90° |
| | c = 10.0751(5) Å | γ = 120° |
| Volume | 7039.7(9) Å³ | |
| Density | 1.398 | |

A) Letermovir sodium trihydrate by invention

B) Letermovir EtOH – water solvate under air, after ca. 1 hour (US2015/0038514 A1)

C) Letermovir sodium trihydrate under air, after ca. 2 weeks (US2015/0038514 A1)

2Theta (Offset coupled TwoTheta/Theta) WL=1.54060

METHOD OF PRODUCING A CRYSTALLINE FORM OF SODIUM 2-[(4S)-8-FLUORO-2-[4-(3-METHOXYPHENYL)PIPERAZIN-1-YL]-3-[2-METHOXY-5-(TRIFLUOROMETHYL) PHENYL]-4H-QUINAZOLINE-4-YL]ACETATE TRIHYDRATE

The present invention refers to an effective method of preparing a crystalline form of sodium 2-[(4S)-8-fluoro-2-[4-(3-methoxyphenyl)piperazin-1-yl]-3-[2-methoxy-5-(trifluoro-methyl)phenyl]-4H-quinazolin-4-yl]acetate trihydrate.

BACKGROUND OF THE INVENTION

Cytomegalovirus (CMV) is a common opportunistic infection that causes significant morbidity and preventable mortality after solid-organ and allogeneic hematopoietic stem cell transplantation.

(S)-(+)-{8-fluoro-2-[4-(3-methoxyphenyl)piperazine-1-yl]-3-[2-methoxy-5-trifluoro-methyl)phenyl]-3,4-dihydro-quinazoline-4-yl}acetic acid or 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid is known as letermovir. It was developed as an antiviral agent, in particular for combating infections caused by the human cytomegalovirus (HCMV) in WO 2004/096778. Salts of 2-[(4S)-8-fluoro-2-[4-(3-methoxyphenyl)piperazin-1-yl]-3-[2-methoxy-5-(trifluoro-methyl)phenyl]-4H-quinazolin-4-yl]acetic acid are obtained in crystalline or amorphous form (WO 2013/127971 A1). Particularly, some sodium or calcium salts of letermovir have been obtained mainly in amorphous form. In case of the sodium salt of letermovir, some crystalline sodium hydrates are also obtained.

There remains a need, however, for an effective method for producing a crystalline form of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate as is evident from the independent claims.

DESCRIPTION OF THE INVENTION

In one aspect, the present invention relates to a crystalline sodium 2-[(4S)-8-fluoro-2-[4-(3-methoxyphenyl)piperazin-1-yl]-3-[2-methoxy-5-(trifluoromethyl)phenyl]-4H-quinazolin yl]acetate trihydrate of formula (I), (I)

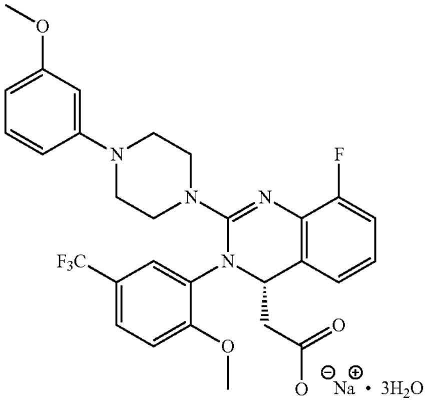

which is essentially free from alcohols, in particular, methanol or ethanol. Alcohols, in particular methanol or ethanol are not involved in any step of preparation of said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate. This results in obtaining the product which does not contain said alcohols.

In another aspect, the present invention relates to a method for producing the crystalline form of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate of formula (I)

(I)

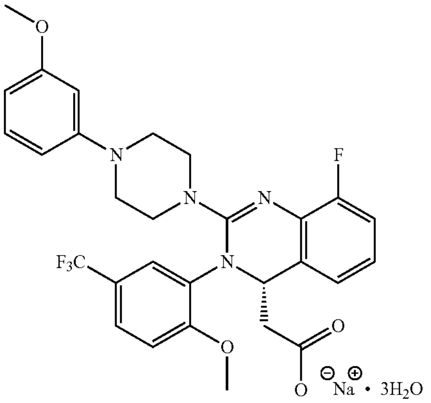

the method comprising the steps:

Step 1) providing a solution of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid in a mixture of a ($C_1$-$C_6$) alkyl acetate and a ($C_1$-$C_6$) dialkyl ether, wherein the molar ratio of ($C_1$-$C_6$) alkyl acetate:($C_1$-$C_6$) dialkyl ether is from 1:1 to 1:3 in a concentration of from 0.3 M to 0.7 M and wherein the temperature of the solution is preferably in the range of from 30° C. to 60° C.;

Step 2) adding 1.0 to 2.0 mole equivalents of an aqueous sodium hydroxide solution based on the 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid content to the solution resulting from step 1 to provide a mixture;

Step 3) stirring the mixture resulting from in step 2 for at least 30 minutes at a temperature in the range of from 30° C. to 60° C. to obtain a suspension containing a solid compound;

Step 4) separating the solid compound from the suspension resulting from step 3; and Step 5) drying the solid compound resulting from step 4 at a temperature in the range of from 30° C. to 60° C. for at least one hour to obtain crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate.

In the method of the prior art, the sodium salt of Letermovir had to be separately produced and then after one week of treatment of said sodium salt in aqueous alcohol, such as methanol or ethanol, a crystalline solid was obtained and filtered off. In the present disclosure, it is proven that said crystalline solid of the prior art is not Letermovir sodium trihydrate, but a mixed alcohol water solvate form of Letermovir.

In case methanol was used as solvent, the crystalline form of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate methanol monohydrate was formed as shown in FIG. 1. Table 1 lists the X-ray structure data of said crystalline letermovir sodium methanol monohydrate.

In case ethanol was used as solvent, the crystalline form of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate ethanol monohydrate was formed as shown in FIG. 2. Table 2 lists the X-ray structure data of said crystalline letermovir sodium ethanol monohydrate.

Said crystals obtained, i.e. letermovir sodium methanol monohydrate and letermovir sodium ethanol monohydrate, have to be dried at room temperature and ambient humidity for two weeks for transformation to the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate as shown in FIG. 4.

Also, the use of water as co-solvent does not result in the formation of letermovir sodium trihydrate. Therefore, there is no successful method for producing letermovir sodium salt trihydrate in the prior art that uses water as co-solvent.

In the present invention, the following parameters are tested during the development and optimization:

- solvent/antisolvent ratio
- addition of antisolvent (rate and moment of addition)
- API concentration
- NaOH addition (direct or dissolved in water)
- water volume
- reaction time
- reaction temperature
- inoculating with seed crystals (optionally)

By the above-described inventive method, the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate of formula (I) is obtained directly by using water as co-solvent.

The method of the present invention has following technical advantages:

- sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate can be prepared directly from letermovir base;
- the overall process requires a relatively short reaction time (4 hours+15 hours for drying);
- the process directly yields letermovir sodium trihydrate (no other transition forms);
- the process is reproducible and scalable.

In another aspect the present invention relates to a pharmaceutical composition comprising said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate and methods of preparation of said pharmaceutical composition.

DETAILED DESCRIPTION

It is noted that the term "comprising" also encompasses the meaning "consisting of", e.g., a group of members comprising said members also encompasses a group of members consisting only of these members.

The term "room temperature" as used herein, is synonymously to the term "standard room temperature" and refers to a temperature between 19° C. and 26° C. For example, "cooling down a suspension to room temperature" means "cooling down a suspension to a temperature in the range of from 19° C. to 26° C.".

As used herein, the term "crystal" refers to any three-dimensional ordered array of molecules that diffracts X-rays.

As used herein, the term "unit cell" refers to a basic parallelepiped shaped block. The entire volume of crystal may be constructed by regular assembly of such blocks.

Each unit cell comprises a complete representation of the unit of pattern, the repetition of which builds up the crystal.

As used herein, the term "space group" refers to the arrangement of symmetry elements of a crystal.

As used herein, the term "asymmetric unit" refers to a minimal set of atomic coordinates that can be used to generate the entire repetition in a crystal.

The term "polymorph" refers to a particular crystal form (i.e. structure of crystal lattice) of potassium salt of letermovir or a solvate thereof that can exist in more than one crystal form in the solid state.

As used herein, the term "solvates" refers to those forms of a compound in particular sodium 2-[(4S)-8-fluoro-2-[4-(3-methoxyphenyl)piperazin-1-yl]-3-[2-methoxy-5-(trifluoro-methyl)phenyl]-4H-quinazolin-4-yl]acetate trihydrate which form a complex through coordination with solvent molecules. Hydrates are a special form of solvates in which the coordination takes place with water.

As used herein, the term "($C_1$-$C_6$) alkyl" refers to saturated, linear or branched, hydrocarbon groups of from 1 to 6 carbon atoms, i.e. the term "($C_1$-$C_6$) alkyl" refers to a linear hydrocarbon group of $—CH_3$, $—C_2H_5$, $—C_3H_7$, $—C_4H_9$, $—O_5H_{11}$, $—C_6H_{13}$, or a branched hydrocarbon group of $—CH(CH_3)_2$, $—CH_2—CH(CH_3)_2$, $—CH(CH_3)—C_2H_5$, $—C(CH_3)_3$, $—CH(CH_3)—C_3H_7$, $—CH_2—CH(CH_3)—C_2H_5$, $—CH(CH_3)—CH(CH_3)_2$, $—C(CH_3)_2—C_2H_5$, $—CH_2—C(CH_3)_3$, $—CH(C_2H_5)_2$, $—C_2H_4—CH(CH_3)_2$, $—C_3H_6—CH(CH_3)_2$, $—C_2H_4—CH(CH_3)—C_2H_5$, $—CH(CH_3)—C_4H_9$, $—CH_2—CH(CH_3)—C_3H_7$, $—CH(CH_3)—CH_2—CH(CH_3)_2$, $—CH(CH_3)—CH(CH_3)—C_2H_5$, $—CH_2—CH(CH_3)—CH(CH_3)_2$, $—CH_2—C(CH_3)_2—C_2H_5$, $—C(CH_3)_2—C_3H_7$, $—C(CH_3)_2—CH(CH_3)_2$, $—C_2H_4—C(CH_3)_3$, or $—CH(CH_3)—C(CH_3)_3$.

As used herein, the term "dialkyl ether" refers to a group of formula R—O—R, wherein each of the R groups is alkyl.

Within the scope of the present invention the terms "obtained by" and "obtainable by" have the same meaning and are used interchangeably.

Within the scope of the present invention the term "equivalents" is understood to mean "molar equivalents".

As used herein the term "essentially free from alcohols, in particular, methanol or ethanol" refers to a content of an alcohol which is less than 1 mole %, preferably less than 0.5 mole % and more preferably less than 0.3 mole % in a unit cell.

As used herein, the term "dry powder" refers to is a solid dosage form which contains mixtures of finally divided drugs or chemicals in a dry form meant for internal or external use. Finally divided drugs or chemicals in a heterogeneous mixture do not exhibit any physicochemical interactions with one another, e.g. association or agglomeration.

As used herein the term "treatment" or "treating" is defined as the application or administration of a therapeutic agent i.e., a trihydrate of sodium salt of letermovir (alone or in combination with another pharmaceutical agent) to a subject, or application or administration of a therapeutic agent to an isolated tissue or cell line from a subject who has an HCMV infection, a symptom of HCMV infection, or the potential to develop an HCMV infection with the purpose to cure, heal, alleviate, relieve, alter, remedy, ameliorate, improve or affect the HCMV infection, the symptoms of HCMV infection or the potential to develop an HCMV infection. Such treatments may be specifically tailored or modified based on knowledge obtained from the field of pharmacogenomics.

As used herein the term "prevent", "preventing" or "prevention" means no disorder or disease development if none had occurred, or no further disorder or disease development if there had already been development of the disorder or disease. Also considered is the ability of one to prevent some or all of the symptoms associated with the disorder or disease. Prevention of diseases also encompasses prophylaxis of diseases.

As used herein the term ""subject" refers to a human or a non-human mammal. Non-human mammals include for example livestock and pets such as ovine, bovine, porcine, feline, canine and murine mammals. Preferably the subject is human.

As used herein the term "pharmaceutically acceptable" refers to a material such as a carrier or diluent which does not abrogate the biological activity or properties of the compound and is relatively non-toxic i.e. the material may be administered to a subject without causing undesirable biological effects or interacting in a deleterious manner with any of the components of the composition in which it is contained.

Preferably, in the method of the present invention, the ($C_1$-$C_6$) alkyl acetate is methyl acetate, propyl acetate, isopropyl acetate or butyl acetate, or a mixture of the aforementioned and the ($C_1$-$C_6$) dialkyl ether is diisopropyl ether, methoxypentane, or methyl tert-butyl ether (MTBE), or a mixture of the aforementioned. More preferably, the ($C_1$-$C_6$) alkyl acetate is isopropyl acetate and the ($C_1$-$C_6$) dialkyl ether is diisopropyl ether.

Preferably in step 1 of the herein-mentioned methods, the concentration of the solution of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid is in the range of 0.3 M to 0.6 M.

Preferably in step 2 of the herein-mentioned methods, the concentration of sodium hydroxide in the aqueous sodium hydroxide solution is in a range of 5 M to 30 M, more preferably in the range of 10 M to 30 M, even more preferably in the range of 10 M to 27 M, and most preferably in the range of 15 M to 25 M.

Preferably in step 2 of the herein-mentioned methods, 1.1 to 1.5 mole equivalents of sodium hydroxide based on the 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid content are added as an aqueous solution at a concentration of sodium hydroxide in the range of from 5 M to 30 M, more preferably in the range of from 10 M to 30 M, even more preferably in the range of from 10 M to 27 M, and most preferably in the range of 15 M to 25 M.

Preferably, in step 3 of the herein-mentioned methods, the mixture is stirred for 1 to 6 hours at a temperature in the range of from 40° C. to 60° C. More preferably, the mixture is stirred for 1 to 6 hours at a temperature in the range of from 45° C. to 55° C. More preferably, the mixture is stirred for 1 to 6 hours at a temperature of 50° C. Preferably, in step 3 the mixture is stirred for 2 to 5 hours at a temperature in the range of from 40° C. to 60° C. More preferably, the mixture is stirred for 2 to 5 hours at a temperature in the range of from 45° C. to 55° C. More preferably, the mixture is stirred for 2 to 5 hours at a temperature of 50° C. Preferably, in step 3 the mixture is stirred for 3 to 4 hours at a temperature in the range of from 45° C. to 55° C. More preferably, the mixture is stirred for 3 to 4 hours at a temperature in the range of from 45° C. to 55° C. More preferably, the mixture is stirred for 3 to 4 hours at a temperature of 50° C.

In one embodiment, step 3 of the inventive method further comprises the subsequent step of cooling down the stirred suspension to room temperature at a cooling rate of 60K per hour or below, filtering the cooled suspension to provide a solid compound, and optionally washing the solid compound with the ($C_1$-$C_6$) dialkyl ether, which is identical to the ($C_1$-$C_6$) dialkyl ether used in step 1.

In a preferred embodiment, the ($C_1$-$C_6$) alkyl acetate is methyl acetate, propyl acetate, isopropyl acetate or butyl acetate, or a mixture thereof and the ($C_1$-$C_6$) dialkyl ether is diisopropyl ether, methoxypentane, or methyl tert-butyl ether, or a mixture thereof, preferably wherein the ($C_1$-$C_6$) alkyl acetate is isopropyl acetate and the ($C_1$-$C_6$) dialkyl ether is diisopropyl ether, and more preferably, wherein the ($C_1$-$C_6$) alkyl acetate is isopropyl acetate and the ($C_1$-$C_6$) dialkyl ether is diisopropyl ether and the molar ratio of isopropyl acetate:dialkyl ether is 1:2.

In one embodiment, the solid compound is dried in step 5 of the herein-mentioned method under reduced pressure below 10 hPa. In a preferred embodiment, the solid compound is dried in step 5 of the herein-mentioned method at around 2 to 3 hPa at 50° C. for 15 hours.

Thus, in a particularly preferred embodiment, another aspect of this invention relates to a method for producing a crystalline form of sodium 2-R4S)-8-fluoro-2-[4-(3-methoxyphenyl)piperazin-1-yl]-3-[2-methoxy-5-(trifluoromethyl)phenyl]-4H-quinazolin-4-yl]acetate trihydrate of formula (I) comprising the steps:

Step 1) providing a solution of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid in a mixture of isopropyl acetate and diisopropyl ether, wherein the molar ratio of isopropyl acetate:diisopropyl ether is from 1:1 to 1:3 in a concentration range of from 0.3 M to 0.6 M, and wherein the temperature of the solution is in the range of from 30° C. to 60° C.;

Step 2) adding 1.1 to 1.5 mole equivalents of an aqueous sodium hydroxide solution based on the 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid content to the solution resulting from step 1, wherein the sodium hydroxide in the aqueous sodium hydroxide solution has a concentration of from 15 M to 25 M to provide a mixture;

Step 3) stirring the mixture resulting from step 2 for 3 to 4 hours at a temperature of 50° C. to obtain a suspension containing a solid compound;

Step 4) cooling down the stirred suspension to room temperature at a cooling rate of 60K per hour or below, filtering the cooled suspension to provide a solid compound, and washing the solid compound with diisopropyl ether; and Step 5) drying the solid compound resulting from step 4 at a temperature in the range of from 30° C. to 60° C. for at least one hour to obtain crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate.

In another embodiment of the herein-mentioned methods step 2 further comprises: inoculating the solution with seed crystals of sodium 2-[(4S)-8-fluoro-2-[4-(3-methoxyphenyl) piperazin-1-yl]-3-[2-methoxy-5-(trifluoromethyl)phenyl]-4H-quinazolin-4-yl]acetate trihydrate in an amount of 0.5-1 wt % based on the total weight of 2-[(4S)-8-fluoro-244-(3-methoxyphenyl)piperazin-1-yl]-3-[2-methoxy-5-(trifluoromethyl)phenyl]-4H-quinazolin-4-yl]acetic acid provided in step 1.

In another embodiment the invention relates to a method producing a crystalline form of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate of formula (I) further comprising the additional subsequent step:

Step 6) micronizing or nanomiling the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate resulting from Step 5) to obtain a pharmaceutical composition comprising the micronized crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate.

In a preferred embodiment the micronized or nanomilled crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate has a particle size in a range of 0.3 to 1000 μm and the particle size distribution is preferably defined by d(0.1) from 1 to 100 μm, d(0.5) from 30 to 250 μm and d(0.9) from 100 to 800 μm and more preferably defined by d(0.1) from 2 to 50 μm, d(0.5) from 25 to 100 μm, d(0.9) from 200 to 600 μm.

In the methods disclosed herein, said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate has a crystal system of trigonal, a space group of R3, and a unit cell dimension of a=28.22 Å, b=28.22 Å, c=9.97 Å, $\alpha$=90±3°, $\beta$=90±3°, and $\gamma$=120±3°.

In the methods disclosed herein, the X-ray diffraction pattern of said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate comprises 2-theta angle values of 6.2, 9.5, 12.4, 15.6, 18.0, 19.0, 21.0, 22.5 and 26.8 degrees, and said 2-theta angle values have a normal deviation of ±0.1°.

In a preferred embodiment of the methods disclosed herein, the X-ray diffraction pattern of said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate comprises 2-theta angle values of 6.2, 9.5, 11.3, 12.4, 12.9, 15.6, 16.5, 16.8, 18.0, 19.0, 20.0, 21.0, 21.6, 21.9, 22.5, 22.8, 23.6, 25.0, 25.2, 26.0, 26.8, 27.3, 27.5 and 26.8 degrees, and said 2-theta angle values have a normal deviation of ±0.1°.

The purity of the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate obtained by any one of the above-mentioned methods is at least 98%, preferred, 99%, more preferred 99.5%, most preferred 99.9%, determined by HPLC.

In another aspect, the invention relates to sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate trihydrate which is obtainable by the method described herein.

In a preferred embodiment, the sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate which is obtainable by the method described herein is essentially free from ethanol.

Said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate may be present in different polymorph forms. Polymorphs are different crystalline forms of the same compound which may have substantially different physicochemical properties, such as solubility, stability and bioavailability. Evaluation of polymorphism of a drug substance plays a crucial role in formulation study because polymorphism may impact drug behavior. For example, rate of dissolution of drug substance impacts the bioavailability of finished products. The solubility, in turn, is dependent on the polymorphic nature of the drug substance. Different polymorphs may have different solubilities and hence the corresponding drug products may have different bioavailabilities.

Different methods for examination of polymorphs can be used. Such methods include microscopy, IR-spectroscopy, Raman spectroscopy, Solid-state NMR, TGA, DSC, XRPD, PDF and other techniques. A combination of different techniques can be applied. In particular, PXRD is a powerful technique for examination of polymorphs. X-rays are reflected from crystals only when the angle between the beam and the planes in the crystal satisfies the Bragg condition. There is an infinite number of possible planes in the crystal. Each molecular repetition gives a unique set of reflections and, therefore, generates a unique pattern, which can be recorded as a spectrum.

However, conventional XRPD analysis yields the average structure of materials, e.g. average positions, displacement parameters and occupancies, and is not able to provide the information about local disorders in the material. For this purpose the Pair Distribution Function (PDF) can be used, which gives the probability of finding an atom at a certain distance from a given atom. The PDF is the Sine-Fourier transform of the total scattering diffraction pattern, which provides the information about average interatomic distances, structural disorders or distortions and average coordination properties. Therefore, the PDF is capable of distinguishing different solid forms of the same compound which are indistinguishable with conventional PXRD analysis. In particular, different amorphous forms which are characterized by different degrees of disorder can be determined by the PDF analysis (Boetker et al. Pharmaceutics 2012, 4, 93-103).

Pharmaceutical Composition

In another aspect, the present invention relates to a pharmaceutical composition which comprises sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate according to formula (I) as described herein.

In a preferred embodiment this pharmaceutical composition is a dry powder.

In another preferred embodiment the pharmaceutical composition according to the invention is essentially free from ethanol.

In another aspect, the invention relates to a method disclosed herein for preparing a pharmaceutical composition comprising sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate trihydrate further comprising the additional subsequent step:

Step 6) micronizing or nanomiling the crystalline sodium 2-[(4S)-8-fluoro-2-[4-(3-methoxyphenyl)piperazin-1- yl]-3-[2-methoxy-5-(trifluoromethyl)phenyl]-4H-quinazolin-4-yl]acetate trihydrate resulting from Step 5) to obtain a pharmaceutical composition comprising the micronized crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate.

In another preferred embodiment the method comprises the additional subsequent step of adding at least one pharmaceutically acceptable carrier, excipient and/or diluent to the crystalline sodium 2-[(4S)-8-fluoro-2-[4-(3-methoxyphenyl)piperazin-1-yl]-3-[2-methoxy-5-(trifluoromethyl) phenyl]-4H-quinazolin-4-yl]acetate trihydrate resulting from step 6).

As pharmaceutically acceptable carriers, excipients and/or diluents can be used carriers such as preferably an inert carrier like lactose, starch, sucrose, cellulose, magnesium stearate, dicalcium phosphate, calcium sulfate, talc, mannitol, ethyl alcohol (liquid filled capsules); suitable binders include starch, gelatin, natural sugars, corn sweeteners, natural and synthetic gums such as acacia, sodium alginate, carboxymethylcellulose, polyethylene glycol and waxes, sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrolidone, and inorganic compounds such as magnesium aluminum silicate; lubricants such as boric acid, sodium benzoate, sodium acetate, sodium chloride, magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine; disintegrating agents (disintegrates) such as starch, methylcellulose, guar gum, modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures; coloring agents, sweetening agents, flavoring agents, preservatives; glidents are for example silicon dioxide and talc; suitable adsorbent are clay, aluminum oxide, suitable diluents are water or water/propylene glycol solutions for parenteral injections, juice, sugars such as lactose, sucrose, mannitol, and sorbitol, starches derived from wheat, corn rice, and potato, and celluloses such as microcrystalline cellulose.

The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate.

The pharmaceutical compositions according to the present invention containing sodium 2-[(4S)-8-fluoro-2-[4-(3-methoxyphenyl)piperazin-1-yl]-3-[2-methoxy-5-(trifluoromethyl)-phenyl]-4H-quinazolin-4-yl]acetate trihydrate according to the present invention as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 weight % of the inventive sodium 2-[(4S)-8-fluoro-2-[4-(3-methoxyphenyl) piperazin-1-yl]-3-[2-methoxy-5-(trifluoromethyl)phenyl]-4H-quinazolin-4-yl]acetate trihydrate of formula (I) as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimize the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The sodium 2-[(4S)-8-fluoro-2-[4-(3-methoxyphenyl) piperazin-1-yl]-3-[2-methoxy-5-(trifluoromethyl)phenyl]-4H-quinazolin-4-yl]acetate trihydrate may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient (s). Capsules with hard shells are typically made of blended of relatively high gel strength gelatins from bones or pork skin. The capsule itself may contain small amounts of dyes, opaquing agents, plasticisers and/or preservatives. Under tablet a compressed or moulded solid dosage form is understood, which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilized in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses, such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances, which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

The inventive sodium letermovir trihydrate exhibits an antiviral effect against representatives of the Herpes viridae group (herpes viruses), above all against the cytomegaloviruses (CMV), in particular against the human cytomegalovirus (HCMV). They are thus suitable for use in methods of treating and preventing diseases, especially infections with viruses, in particular the viruses referred to herein and the infectious diseases caused by them. The term "virus infection" is understood here to mean not only an infection with a virus but also a disease caused by infection with a virus In another aspect the invention relates to a pharmaceutical composition which can be obtained by the method described herein.

In another preferred embodiment said pharmaceutical composition can be obtained by said method further comprising the subsequent additional step of adding at least one pharmaceutically acceptable carrier, excipient and/or diluent to the crystalline sodium 2-[(4S)-8-fluoro-2-[4-(3-methoxyphenyl)piperazin-1-yl]-3-[2-methoxy-5-(trifluoromethyl) phenyl]-4H-quinazolin-4-yl]acetate trihydrate.

In a preferred embodiment said pharmaceutical composition comprises crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate, wherein the particle size of said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate trihydrate is in the range of from 0.3 to 1000 μm and the particle size distribution is preferably defined by d(0.1) from 1 to 100 μm, d(0.5) from 30 to 250 μm and d(0.9) from 100 to 800 μm and more preferably the particle size distribution is defined by d(0.1) from 2 to 50 μm, d(0.5) from 25 to 100 μm, d(0.9) from 200 to 600 μm.

The parameter d(0.1) refers to the mesh size of a single notional sieve allowing 10% of the total of all particles of the sample to pass. Thus d(0.1)=2-100 μm means that the upper limit of the particle size range defining the 10% of smallest particles in the sample is between 2 μm to 100 μm. Thus 10% of the total particles have a particle size of not more than d(0.1) meaning in this case that they have a maximum size of 2 μm to 100 μm.

Accordingly, the parameter d(0.5) refers to the mesh size of a single notional sieve allowing 50% of the total of all particles of the sample to pass. Thus d(0.5)=30-250 μm means that the upper limit of the particle size range defining the notional half of the sample containing the smaller particles is between 30 μm to 250 μm. Thus 50% of the total of all particles have a particle size of not more than d(0.5) meaning in this case that they have a maximum size of 30 μm to 250 μm.

Accordingly, the parameter d(0.9) refers to the mesh size of a single notional sieve allowing 90% of the total of all particles of the sample to pass i.e. only 10% of the sample is retained. Thus d(0.9)=100-800 μm means that the lower limit of the particle size range defining the 10% of largest particles in the sample is between 100 μm to 800 μm. Thus 90% of all particles have a particle size of not more than d(0.9) meaning in this case that they have a maximum size of 100 μm to 800 μm.

Preferably, the antiviral agents used in the pharmaceutical compositions of the present invention are effective against viruses of Herpesviridae, particularly cytomegalovirus (CMV) and especially the human cytomegalovirus (HCMV).

Preferably, said pharmaceutical composition further comprises pharmaceutically acceptable carriers, excipients and/or diluents.

Said pharmaceutical composition is preferably administered orally or intravenously.

The inventive sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate exhibits an antiviral effect against representatives of the Herpes viridae group (herpes viruses), above all against the cytomegaloviruses (CMV), in particular against the human cytomegalovirus (HCMV). It is thus suitable for use in methods of treating and preventing diseases, especially infections with viruses, in particular the viruses referred to herein and the infectious diseases caused by them. The term "virus infection" is understood here to mean not only an infection with a virus but also a disease caused by infection with a virus.

Thus, another aspect of this invention refers to a pharmaceutical composition comprising the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate for use in a method of treatment and/or prevention of infectious diseases caused and/or associated by cytomegalovirus, particularly human cytomegalovirus.

Further, the invention relates to the pharmaceutical composition comprising the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate for the preparation of a medicament for the treatment and/or prevention of diseases, in particular of virus infections, preferably human cytomegalovirus (HCMV) infections or infections with another member of the herpes viridae group.

Further, the invention provides a method of treating and/or preventing of a disease associated and/or caused by cytomegalovirus (CMV), particularly human cytomegalovirus (HCMV), or infections with another member of the herpes viridae group which comprises administering to said subject a therapeutically effective amount of the pharmaceutical composition comprising the crystalline sodium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate trihydrate.

The term "effective amount" means an amount of compound that, when administered to a subject in need of such treatment, is sufficient to (i) treat or prevent a particular disease, condition, or disorder;

(ii) attenuate, ameliorate, or eliminate one or more symptoms of the particular disease, condition, or disorder; or (iii) prevent or delay the onset of one or more symptoms of the particular disease, condition, or disorder described herein.

The amount of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate that will correspond to such an amount will vary depending upon factors such as the particular compound, disease condition and its severity, the identity (e.g., weight) of the subject in need of treatment, but can nevertheless be routinely determined by one skilled in the art.

Abbreviations h hour(s)
DSC differential scanning calorimetry
HPLC high pressure liquid chromatography
min. minutes
NMR nuclear magnetic resonance
PDF pair distribution function
TGA thermogravimetric analysis
PXRD Powder X-ray diffraction

Figure 1:
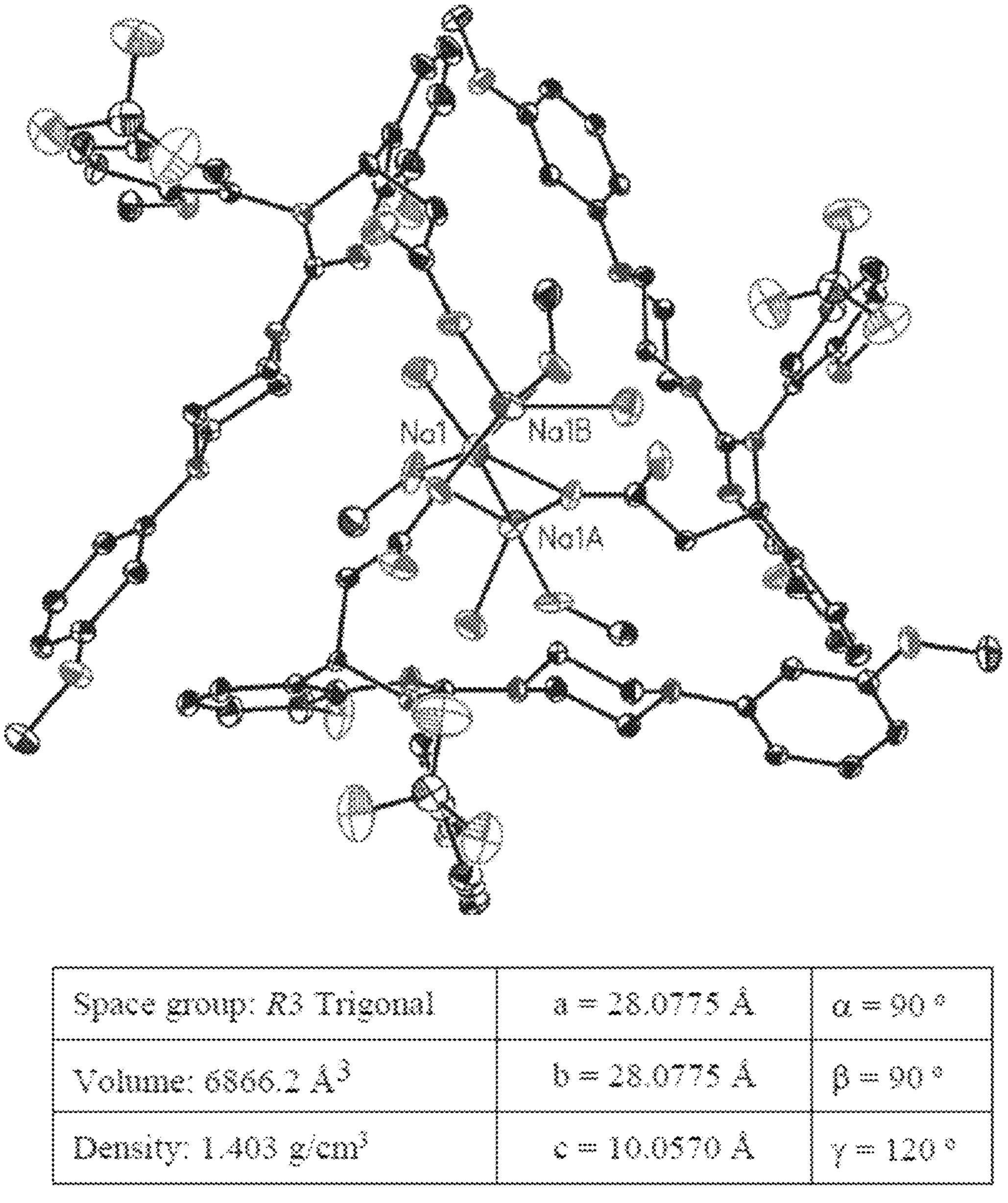
FIG. 1 shows the crystal structure of letermovir sodium methanol monohydrate.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Equipment Used

Powder X-Ray Diffraction analysis (PXRD): Approximately 20 mg of sample were prepared in standard sample holders using two foils of polyacetate. The samples were analysed as received without further manipulation. Powder diffraction patterns were acquired on a D8 Advance Series 2Theta/Theta powder diffraction system using CuKα1-radiation (1.54060 Å) in transmission geometry at room temperature. The system is equipped with a VÅNTEC-1 single photon counting PSD, a Germanium monochromator, a ninety positions autochanger sample stage, fixed divergence slits and a radial soller. The generator intensity for the generation of the X-ray beam is set to 40 mA and 40 kV. Programs used: Data collection with DIFFRAC plus XRD Commander V.2.5.1, and evaluation with EVA V.14.0.0.0 (Bruker-AXS 1996-2007). The patterns were collected in thirty minutes measurements in a range from 4 to 40° in 2Θ (step size 0.049°).

Proton nuclear magnetic resonance spectroscopy (1H-NMR): Proton nuclear magnetic resonance analyses were recorded in deuterated DMSO (DMSO-d6) in a Bruker Avance 400 Ultrashield NMR spectrometer. Spectra were acquired solving 8-10 mg of sample in 0.7 mL of deuterated solvent.

Differential scanning calorimetry analysis (DSC): DSC analyses were recorded in a Mettler Toledo DSC822 with a 56-point Au—AuPd thermopile FRSS sensor. Approximately 2-3 mg of sample were weighed (using a MX5 Mettler Toledo microbalance) into 40 µL aluminium crucibles with a pinhole lid and heated at 10 and/or 20° C./min from 30° C. to 300° C. under nitrogen (50 mL/min). Programs used: Data collection and evaluation with software STARe.

Thermogravimetric analysis (TGA): Thermogravimetric analyses were recorded in a Mettler Toledo TGA/SDTA851 with a balance MT1 type. Approximately 3-4 mg of sample were weighed (using a MX5 Mettler Toledo microbalance) into 40 µL aluminium crucibles with a pinhole lid and heated under nitrogen (10 mL/min) at 10° C./min from 30° C. to 300° C. Programs used: Data collection and evaluation with software STARe.

Single Crystal X-Ray Diffraction (SCXRD):

The measured crystals were prepared under inert conditions immersed in perfluoropolyether as protecting oil for manipulation. Crystal structure determinations were carried out using a Apex DUO Kappa 4-axis goniometer equipped with an APPEX 2 4K CCD area detector, a Microfocus Source E025 IuS using $MoK_\alpha$ radiation (0.71073 Å), Quazar MX multilayer Optics as monochromator and an Oxford Cryosystems low temperature device Cryostream 700 plus (T=−173° C.). Full-sphere data collection was used with ω and φ scans. Programs used: Data collection APEX-2 (Data collection with APEX II v2014.9-0. Bruker (2014). Bruker AXS Inc., Madison, Wisconsin, USA), data reduction Bruker Saint (Data reduction with Bruker SAINT+ version V8.35A. Bruker (2013). Bruker AXS Inc., Madison, Wisconsin, USA) V/.60A and absorption correction SADABS (SADABS: V2014/5 Bruker (2001). Bruker AXS Inc., Madison, Wisconsin, USA. Blessing, Acta Cryst. (1995) A51 33-38).

Structure Solution and Refinement: Crystal structure solution was achieved using the computer program SHELXT (SHELXT; Sheldrick, G. M. Acta Cryst. 2015 A71, 3-8). Visualization was performed with the program SHELXIe (SHELXIe; C. B. Huebschle, G. M. Sheldrick & B. Dittrich; J.Appl.Cryst. (2011) 44, 1281-1284). Missing atoms were subsequently located from difference Fourier synthesis and added to the atom list. Least-squares refinement on F2 using all measured intensities was carried out using the program SHELXL 2015 (SHELXL; Sheldrick, G. M. Acta Cryst. 2015 C71, 3-8. SHELXT.). All non-hydrogen atoms were refined including anisotropic displacement parameters.

Comparative Example 01: Monosodium Salt of 2-[(4S)-8-fluoro-2-[4-(3-methoxy-phenyl)piperazin-1-yl]-3-[2-methoxy-5-(trifluoromethyl)phenyl]-4H-quinazolin-4-yl]acetic acid (corresponds to Example 1 of US 2015/0038514 A1)

333.1 g of 2-[(4S)-8-fluoro-2-[4-(3-methoxyphenyl)piperazin-1-yl]-3-[2-methoxy-5-(trifluoro-methyl)phenyl]-4H-quinazolin-4-yl]acetic acid are dissolved in 1300 mL of a mixture of ethanol and diisopropyl ether (1:1) in a 2000 mL three-neck flask. 21.9 g (546.84 mmol) of NaOH are added as a solid to the solution. The mixture is heated for 25 min. to an inner temperature of 50° C., and this yields a clear orange-coloured solution. The solution thus obtained is stirred for 3 hours at this temperature, and a thin suspension is formed already after 1 hour. The reaction mixture is then cooled down for 10 hours at a cooling rate of 3° C./hour to an inner temperature of 20° C. and then stirred for a further 5 hours at this temperature. The total volume of the reaction mixture is reduced under vacuum to approximately 750 mL and the suspension obtained in this way is stirred at 20° C. for 2 hours. Next, 250 mL diisopropyl ether is added over a period of 10 min to the reaction mixture obtained and the mixture is stirred for further 2 hours. The crystalline product which is obtained is vacuumed off by a suction device, washed 2× within each case 250 mL diisopropyl ether, and dried in a vacuum drying cabinet for 20 hours at 20° C. and 160 mbar. The crystalline solid obtained in this way is then dried for 10 min. at 90° C. in an IR dryer and then again for further 16 hours at 60° C. in the vacuum drying cabinet. In this way a total of 274.4 g (86% of the theoretical yield) of the desired crystalline sodium salt is obtained.

Comparative Example 02: Production of the Trihydrate of the Monosodium Salt of 2-[(4S)-8-fluoro-2-[4-(3-methoxyphenyl)piperazin-1-yl]-3-[2-methoxy-5-(trifluoro-methyl)phenyl]-4H-quinazolin-4-yl]cetic acid (modification of Example 2 in US 2015/0038514 A1)

About 300 mg of the sodium salt of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid obtained from Comparative Example 1 are suspended in 1 mL methanol or ethanol (containing 4% water) and shaken for a week at 25° C. The crystalline obtained is filtered off and the residue is dried at room temperature and ambient humidity for two weeks. The residue obtained corresponds to the title compound as trihydrate.

The solid obtained is filtered off after shaking in the respective given solvent for one week at 20° C., the following crystals were obtained.

In case methanol was used as solvent, crystals of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate methanol monohydrate were obtained as shown in FIG. 1. Table 1 lists the X-ray structure data of said crystalline letermovir sodium methanol monohydrate.

Figure 2:
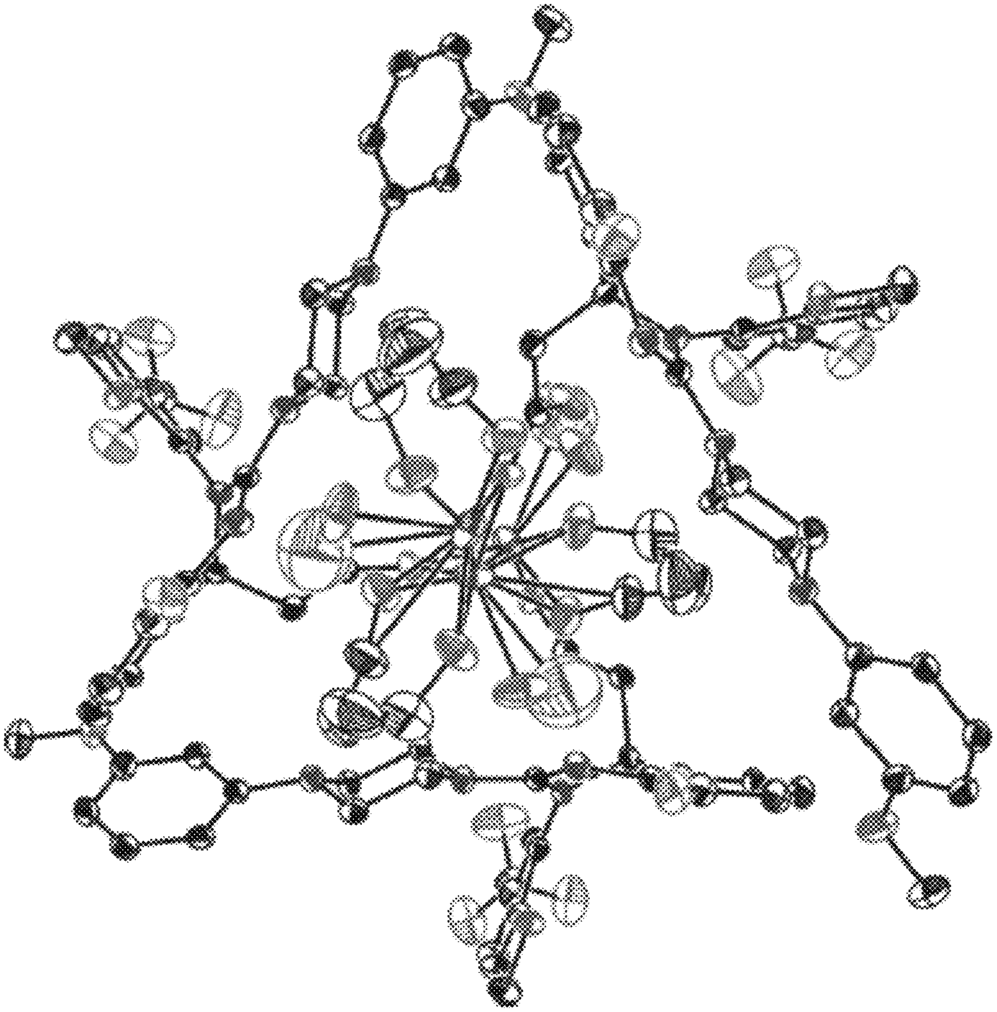
FIG. 2 shows the crystal structure of letermovir sodium ethanol monohydrate.

In case ethanol was used as solvent, crystals of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate ethanol monohydrate were obtained as shown in FIG. 2. Table 2 lists the x-ray structure data of said crystalline letermovir sodium ethanol monohydrate.

The asymmetric unit contains one anionic molecule, one sodium cation, one water molecule and one ethanol molecule. The water and the ethanol molecule, which are coordinated to the sodium cation, are disordered in two positions (ratio 60:40). This compound crystallizes in the chiral space group R3 but a determination of the absolute structure could not be performed. The structure obtained by using ethanol is isostructural to the structure obtained using methanol. The structure is of high quality with a $R_1$ value of 4.75%.

Figure 3:
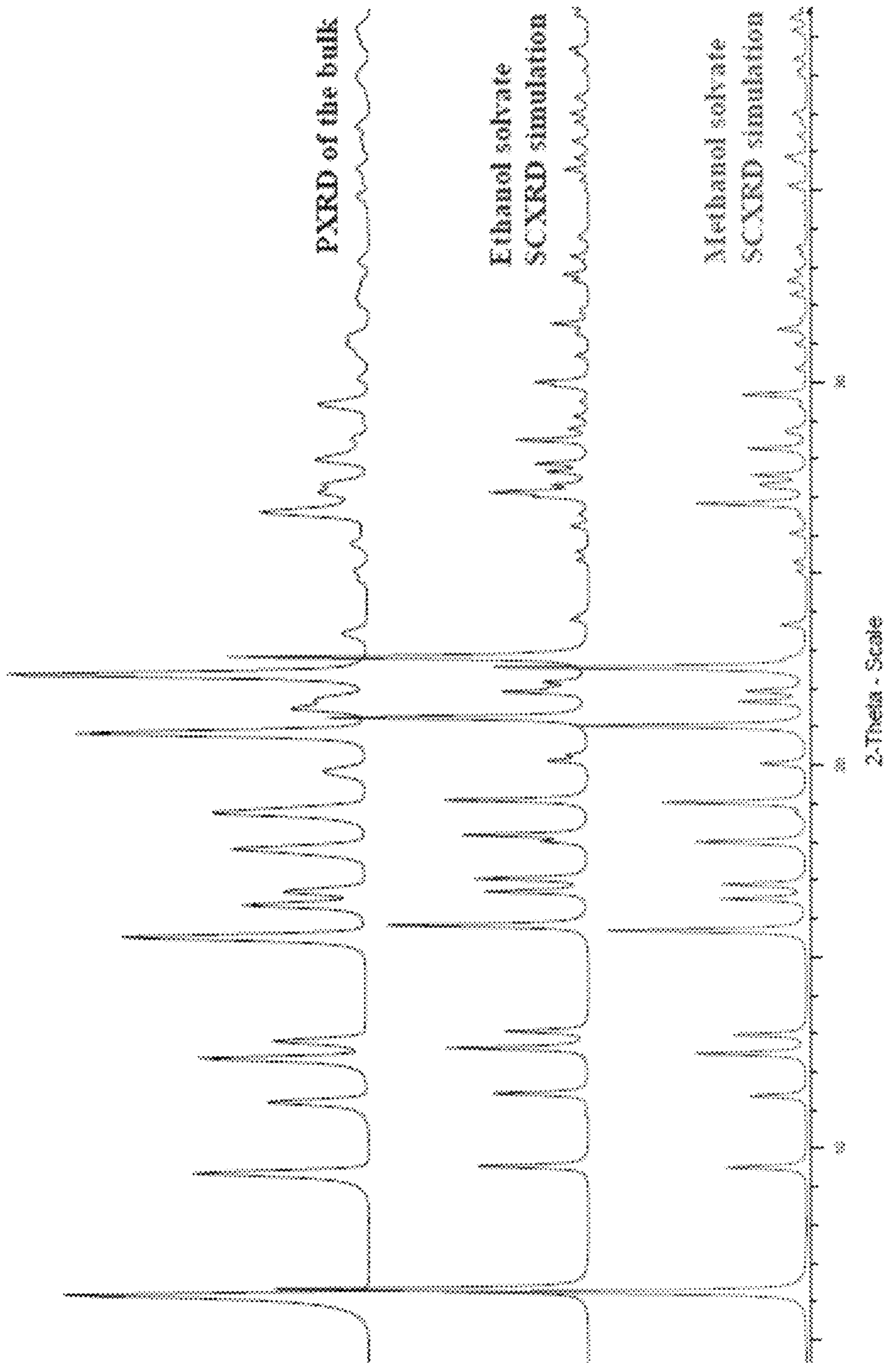
FIG. 3 shows a PXRD comparison of the letermovir sodium methanol monohydrate (water) solvate from the SCXRD simulation (in red), Letermovir sodium ethanol monohydrate (water) solvate from the SCXRD simulation (in blue) and the PXRD pattern of the bulk (in black).

FIG. 3 shows a comparison of the PXRD patterns of both solvates (from the SCXRD simulation) and the PXRD pattern of the bulk. The three samples have very similar patterns (isomorph).

Figure 4:
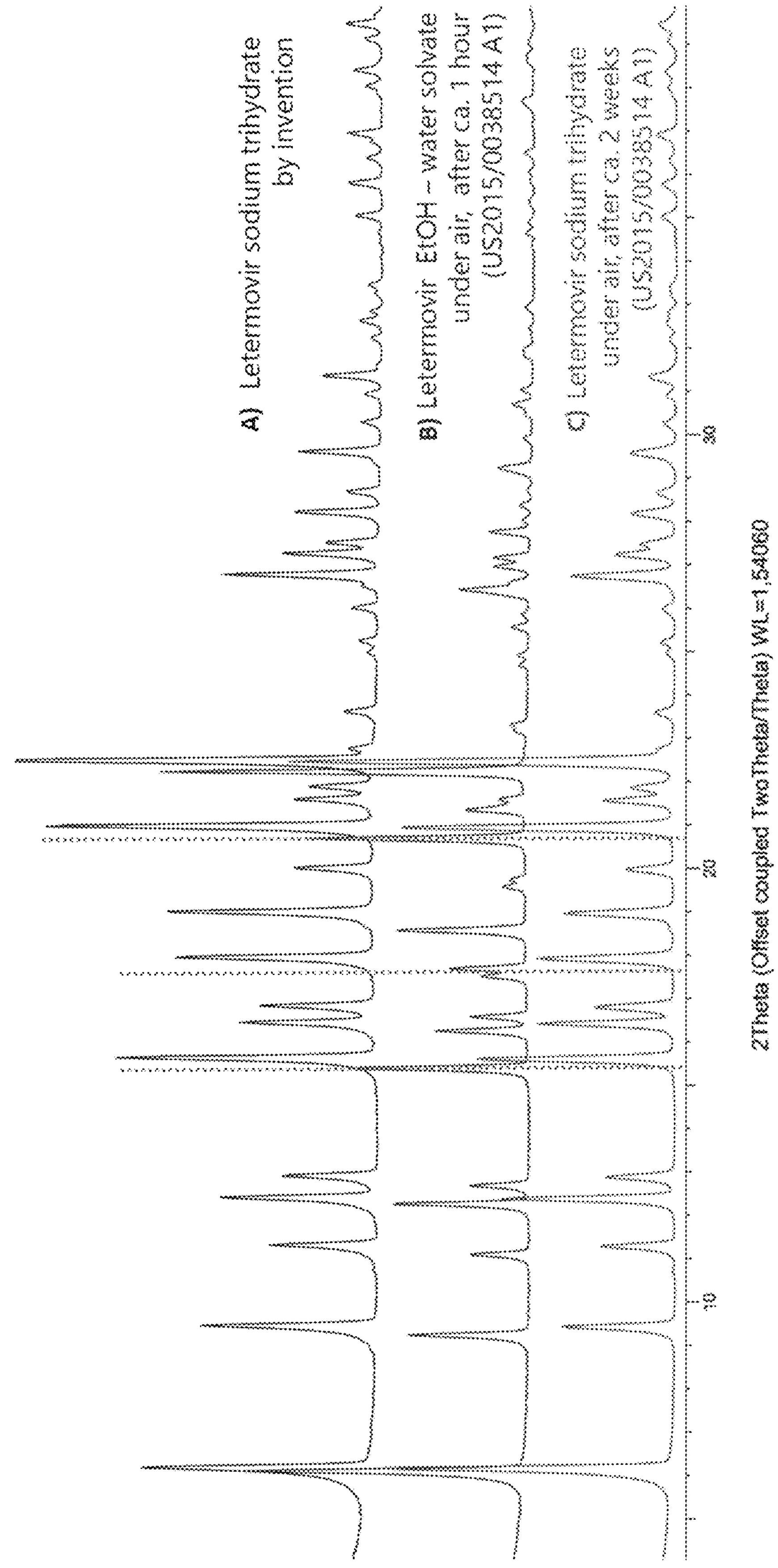
FIG. 4 shows a PXPD comparison of the letermovir sodium trihydrate from the present invention (in black), letermovir sodium ethanol monohydrate (water) solvate after air drying for 1 hour after filtering (in blue) and letermovir sodium trihydrate after air drying for 2 weeks after filtering (in red).

Said crystals obtained, i.e. crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl] acetate methanol monohydrate or crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate ethanol monohydrate, have to be dried at room temperature and ambient humidity for two weeks for transformation to the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate as shown in FIG. 4.

TABLE 1

The crystal data and structure refinement for the crystalline of letermovir sodium methanol monohydrate as shown in FIG. 1.

| | | |
|---|---|---|
| Identification code | mo_P0770INOHEOHLT_0m | |
| Empirical formula | C30 H33 F4 N4 Na O6 | |
| Formula weight | 644.59 | |
| Temperature | 100(2) K | |
| Wavelength | 0.71073 Å | |
| Crystal system | Trigonal | |
| Space group | R3 | |
| Unit cell dimensions | a = 28.0775(12) Å | α = 90° |
| | b = 28.0775(12) Å | β = 90° |
| | c = 10.0570(4) Å | γ = 120° |
| Volume | 6866.2(6) Å$^3$ | |
| Z | 9 | |
| Density (calculated) | 1.403 Mg/m$^3$ | |
| Absorption coefficient | 0.126 mm$^{-1}$ | |
| F(000) | 3024 | |
| Crystal size | 0.40 × 0.40 × 0.20 mm$^3$ | |
| Theta range for data collection | 1.450 to 30.511°. | |
| Index ranges | −20 ≤ h ≤ 39, −38 ≤ k ≤ 37, −10 ≤ l ≤ 13 | |
| Reflections collected | 13982 | |
| Independent reflections | 6646[R(int) = 0.0381] | |
| Completeness to theta = 30.511° | 96.3% | |
| Absorption correction | Multi-scan | |
| Max. and min. transmission | 0.975 and 0.76 | |
| Refinement method | Full-matrix least-squares on F$^2$ | |
| Data/restraints/parameters | 6646/87/451 | |
| Goodness-of-fit on F$^2$ | 1.051 | |
| Final R indices [I > 2sigma(I)] | R1 = 0.0430, wR2 = 0.1104 | |
| R indices (all data) | R1 = 0.0504, wR2 = 0.1181 | |
| Flack parameter | x = −0.2(3) | |
| Largest diff. peak and hole | 0.314 and −0.345 e · Å$^{-3}$ | |

TABLE 2

The crystal data and structure refinement for the crystalline of letermovir sodium ethanol monohydrate as shown in FIG. 2.

| | | |
|---|---|---|
| Identification code | mo_P0770INOHEOH_0m | |
| Empirical formula | C31 H35 F4 N4 Na O6 | |
| Formula weight | 658.62 | |
| Temperature | 100(2) K | |
| Wavelength | 0.71073 Å | |
| Crystal system | Trigonal | |
| Space group | R3 | |
| Unit cell dimensions | a = 28.4046(16) Å | α = 90° |
| | b = 28.4048(16) Å | β = 90° |
| | c = 10.0751(5) Å | γ = 120° |
| Volume | 7039.7(9) Å$^3$ | |
| Z | 9 | |
| Density (calculated) | 1.398 Mg/m$^3$ | |
| Absorption coefficient | 0.124 mm$^{-1}$ | |
| F(000) | 3096 | |
| Crystal size | 0.20 × 0.20 × 0.10 mm$^3$ | |
| Theta range for data collection | 2.184 to 30.652°. | |
| Index ranges | −40 ≤ h ≤ 20, −40 ≤ k ≤ 28, −12 ≤ l ≤ 10 | |
| Reflections collected | 13091 | |
| Independent reflections | 7753[R(int) = 0.0182] | |
| Completeness to theta = 30.511° | 95.3% | |
| Absorption correction | Multi-scan | |
| Max. and min. transmission | 0.988 and 0.947 | |
| Refinement method | Full-matrix least-squares on F$^2$ | |
| Data/restraints/parameters | 7753/133/462 | |
| Goodness-of-fit on F$^2$ | 1.029 | |
| Final R indices [I > 2sigma(I)] | R1 = 0.0475, wR2 = 0.1192 | |
| R indices (all data) | R1 = 0.0531, wR2 = 0.1239 | |
| Flack parameter | x = 0.13(15) | |
| Largest diff. peak and hole | 0.794 and −0.413 e · Å$^{-3}$ | |

Example 01: Direct Preparation of the Crystalline Sodium 2-[(4S)-8-fluoro-2-[4-(3-methoxyphenyl) piperazin-1-yl]-3-[2-methoxy-5-(trifluoromethyl) phenyl]-4H-quinazolin-4-yl]acetate trihydrate and Optimization Experiments 1. Development, 2 Gram Scale The development at a 2 gram scale was performed in reaction tubes. In light of the previous results, NaOH was added as an aqueous, concentrated solution, and the addition of antisolvent was controlled.

As antisolvent, diisopropyl ether was selected as the main antisolvent in the performed reactions.

Solvent: As proven in Comparative Example 02 performed according to the prior art (WO 2013/127971), letermovir sodium forms a significant number of solvates, particularly with alcohols such as methanol and ethanol. Thus, use of alcohols and other solvents which may promote the formation of solvates other than sodium trihydrate were excluded in the present development.

Other Parameters

The following parameters were modified during the development and optimization:

solvent/antisolvent ratio addition of antisolvent (rate and moment of addition)

API concentration

NaOH addition (direct or dissolved in water)

water volume reaction time reaction temperature inoculation with crystal seeds

A summary of the performed experiments is available in Table 3. The results suggest that the reduction in the water volume seems to positively affect the outcome of the reaction. The rate of addition of the antisolvent does not appear to significantly affect the procedure. The obtained yields were, generally, average to low. Whereas diisopropylether was found to be the most reliable antisolvent, all solvents afford comparable results.

Based on the experimental results depending on the methodology variables, the most critical reaction parameters were selected for a series of optimization experiments.

TABLE 3

Reactions performed in the crystallization development of letermovir sodium trihydrate (2 gram scale).

| Solvent | Solvent Volume | Antisolvent Volume | Conc (solv) Conc (total) | NaOH (water) | Temp. Duration | Seeding | Yield |
|---|---|---|---|---|---|---|---|
| AET | 2 + 2 mL | 2 + 5 mL | 0.5 g/mL 0.18 g/mL | 0.5 mL (280 mg/mL) | 50° C. (2 h) r.T. (15 h) | Yes | 52% |
| AET | 4 mL | 4 + 8 mL | 0.5 g/mL 0.13 g/mL | 0.2 mL (700 mg/mL) | 50° C. (2 h) r.T. (15 h) | Yes | 75% |
| MAC | 3 mL | 5 + 5 + 5 mL (syr.pump) | 0.7 g/mL 0.11 g/mL | 0.2 mL (700 mg/mL) | 50° C. (2 h) r.T. (15 h) | Yes | 72% |
| MEC | 4 mL | 4 + 8 mL | 0.5 g/mL 0.13 g/mL | 0.2 mL (700 mg/mL) | 50° C. (2 h) r.T. (15 h) | Yes | 88% |
| MEC | 2 + 1 mL | 8 mL (syr.pump) | 0.7 g/mL 0.18 g/mL | 0.2 mL (700 mg/mL) | 50° C. (2 h) r.T. (15 h) | Yes | 37% |
| MEC | 3 mL | 5 + 5 + 5 mL (syr.pump) | 0.7 g/mL 0.11 g/mL | 0.2 mL (700 mg/mL) | 50° C. (2 h) r.T. (4 h) | Yes | 30% |

AET = ethyl acetate, AIP = isopropyl acetate, MAC = methyl acetate, MEC = methyl ethyl ketone, Antisolvent = diisopropyl ether.

2. Further Optimization

The results of the development experiments outlined the following critical factors:

API concentration solvent/antisolvent ratio antisolvent addition water volume

The optimization was aimed to obtain a robust methodology which can be easily scaled up. Thus, experiments were performed in a 10 to 20 g scale, using an EasyMax™. Results are available in Table 4. Experiments performed in the EasyMax™ unveiled some issues which had not been observed at smaller scales.

TABLE 4

Reactions performed in the crystallization development of letermovir sodium trihydrate in 10-20 gram scale.

| Scale | Solvent | Solvent Volume | Antisolvent Volume | Conc (solv) Conc (total) | NaOH (water) | Temp. Duration | Seeding | Yield |
|---|---|---|---|---|---|---|---|---|
| 10 g | AET | 15 mL | 25 + 25 mL (syr.pump) | 0.7 g/mL 0.15 g/mL | 0.7 mL (1 g/mL) | 50° C. (1 hour) 50-20° C. (2 hour) 20-5° C. (1 hour) | Yes (<0.5%) | 88% |
| 10 g | AET | 15 mL | 15 + 15 mL | 0.7 g/mL 0.22 g/mL | 0.75 mL (1 g/mL) | 50-35° C. (1 h) 35° C. (1 h) 50° C. (1 h) 50-5° C. (1.5 h) | Yes (<0.5%) | 62% |
| 20 g | AET | 20 mL | 40 mL | 1 g/mL 0.33 g/mL | 2 mL (1 g/mL) | 50° C. (4 hours) 50-20° C. (1 hour) | Yes (0.5%) | 98% |

TABLE 4-continued

| Reactions performed in the crystallization development of letermovir sodium trihydrate in 10-20 gram scale. | | | | | | | | |
|---|---|---|---|---|---|---|---|---|
| Scale | Solvent | Solvent Volume | Antisolvent Volume | Conc (solv)<br>Conc (total) | NaOH (water) | Temp.<br>Duration | Seeding | Yield |
| 20 g | AIP | 20 mL | 40 mL | 1 g/mL<br>0.33 g/mL | 2 mL<br>(1 g/mL) | 50° C. (4 hours)<br>50-20° C. (1 hour) | Yes<br>(0.5%) | 99% |
| 10 g | MAC | 15 mL | 15 + 15 mL | 0.7 g/mL<br>0.22 g/mL | 0.75 mL<br>(1 g/mL) | 50° C. (4 h)<br>50-20° C. (2 h) | Yes<br>(<0.5%) | 70% |
| 20 g | MAC | 20 mL | 20 + 20 + 20 mL | 1 g/mL<br>0.25 g/mL | 1.5 mL<br>(1 g/mL) | 50° C. (1 hour)<br>50-20° C. (1 hour)<br>50° C. (1 hour) | Yes<br>(<0.5%) | 93% |
| 20 g | MAC | 20 mL | 40 mL | 1 g/mL<br>0.33 g/mL | 2 mL<br>(1 g/mL) | 50° C. (4 hours)<br>50-20° C. (1 hour) | Yes<br>(0.5%) | 74% |
| 10 g | MEC | 15 mL | 15 + 15 mL<br>(syr.pump) | 0.7 g/mL<br>0.22 g/mL | 0.75 mL<br>(1 g/mL) | 50° C. (2 h)<br>50-10° C. (2 h)<br>r.T (15 h) | Yes<br>(<0.5%) | ~99% |
| 20 g | MEC | 20 mL | 40 + 10 mL | 1 g/mL<br>0.29 g/mL | 2 mL<br>(1 g/mL) | 50° C. (1 hour)<br>50-20 C. (2 hour)<br>20-5° C. (1 hour) | Yes<br>(<0.5%) | ~99% |
| 20 g | MEC | 20 mL | 40 mL | 1 g/mL<br>0.33 g/mL | 2 mL<br>(1 g/mL) | 50° C. (4 hours)<br>50-20° C. (1 hour) | Yes<br>(0.5%) | 59% |

AET = ethyl acetate, AIP = isopropyl acetate, MAC = methyl acetate, MEC = methyl ethyl ketone, Antisolvent = diisopropyl ether.

The following parameters were optimized:

- A more concentrated NaOH solution was used (1 g/mL in water). NaOH was added in excess (1.5 mole equivalents)
- More concentrated API solutions were used (ca. 0.33 g/mL)
- The stir rate was medium to vigorous (poor stirring may lead to the formation of oils, resins and biphasic systems)
- Diisopropyl ether was added at different times and rates, with no visible improvements in the outcome
- Reaction was streamlined by dissolving the API in a solvent/antisolvent mixture before NaOH addition
- Optionally, in order to better induce letermovir sodium trihydrate precipitation, the initial solution+base was inoculated with a 0.5 wt % of letermovir sodium trihydrate crystal seeds
- Isopropyl acetate was found to be the most suitable solvent in the optimized reaction conditions; its use affords highly crystalline letermovir sodium trihydrate in quantitative yields Based on the optimized parameters, a general procedure for the preparation of letermovir sodium trihydrate is outlined.

2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid (letermovir) is dissolved in a 1:2 mixture of isopropyl acetate and diisopropylether at 50° C. (final API concentration: 0.33 g/mL). Then, 1.5 mole equivalents of NaOH (1 g/mL aqueous solution) are added and the solution is seeded with letermovir sodium trihydrate A (1-0.5% w/w) and allowed to stir for 4 hours at 50° C. The suspension is then cooled down gradually (50° C. to 20° C. in 1 hour). The contents of the reactor are filtered under vacuum, washed thrice with diisopropyl ether and dried under reduced pressure (2-3 hPa) at 50° C. for 15 hours. A white, compact powder (letermovir sodium trihydrate) is obtained.

The technical features of letermovir sodium ethanol monohydrate (water) and letermovir sodium trihydrate are summarized below.

TABLE 5

| | Ethanol/Water Solvate | Trihydrate |
|---|---|---|
| Preparation method | Reaction crystallization in an ethanol/diisopropylether mixture | Reaction crystallization in an isopropyl acetate/diisopropyl ether mixture |
| Macroscopic aspect of the solid | White Powder | White Powder |
| Optical microscopy | Crystalline solid | Crystalline solid |
| PXRD | Similar crystalline phases; peaks are slightly shifted, some clear differences | |
| SCXRD | 1 Letermovir molecule<br>1 Sodium atom<br>1 Ethanol molecule<br>1 Water moleculee; | 1 Letermovir molecule<br>1 Sodium atom<br>3 Water molecules |

TABLE 5-continued

| | Ethanol/Water Solvate | Trihydrate |
|---|---|---|
| TGA | 1.6% loss of mass between 30 and 100° C.<br>6.3% loss of mass between 100 and 150° C.<br>Decomposition occurs at ca. 250° C. | 3.8% loss of mass between 30 and 100° C.<br>3.8% loss of mass between 100 and 150° C.<br>Decomposition occurs at ca. 250° C. |
| DSC | Weak endotherm between 30 and 80° C.<br>Strong endotherm between 100 and 150° C. | Weak endotherm between 75 and 105° C.<br>Strong endotherm (or two overlapping endotherms) between 105 and 140° C. |
| Hygroscopicity (DVS) | 3.2% water adsorption (10-90% RH)<br>5.3% water adsorption (10-80% RH)<br>PXRD after experiment: trihydrate | 8.6% water adsorption (10-90% RH)<br>4.1% water adsorption (10-80% RH)<br>No PXRD changes after experiment |
| Additional info | The solid turns into the amorphous form in a drying process (>60° C.).<br>The trihydrated form cannot be obtained in a drying process | The solid turns into the amorphous form in a drying process (>60° C.) |

Example 02. Preparation of Sodium 2-[(4S)-8-fluoro-2-[4-(3-methoxyphenyl)pi-perazin-1-yl]-3-[2-methoxy-5-(trifluoromethyl)phenyl]-4H-quinazolin-4-yl]acetate trihydrate in 500 g Scale 499 g of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid are dissolved in a 1:2 mixture of isopropyl acetate and diisopropyl ether at 50° C. (0.75 L/1.5 L), followed by addition of ca. 1.5 equivalents of NaOH (aqueous solution, 1 g/mL, 50 mL) and the solution is seeded with sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate (0.5-1% w/w with respect to the base). The suspension is stirred for 4 hours at 50° C. (stir rate: 150 rpm, glass anchor shaft). Abundant white solid precipitates within the first hour. The reactor is gradually cooled down (50° C. to 20° C. in 1 hour) and its contents are filtered under vacuum and washed thrice with diisopropyl ether. The obtained white solid is dried under reduced pressure (2-3 mBar) at 50° C. for 15 hours.

510 g of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid trihydrate have been obtained.

Example 03. Preparation of Single Crystal of Letermovir Sodium Trihydrate

The crystal was obtained via partial evaporation of a concentrated Letermovir Sodium solution in an isopropyl acetate/diisopropyl ether mixture.

Figure 5:
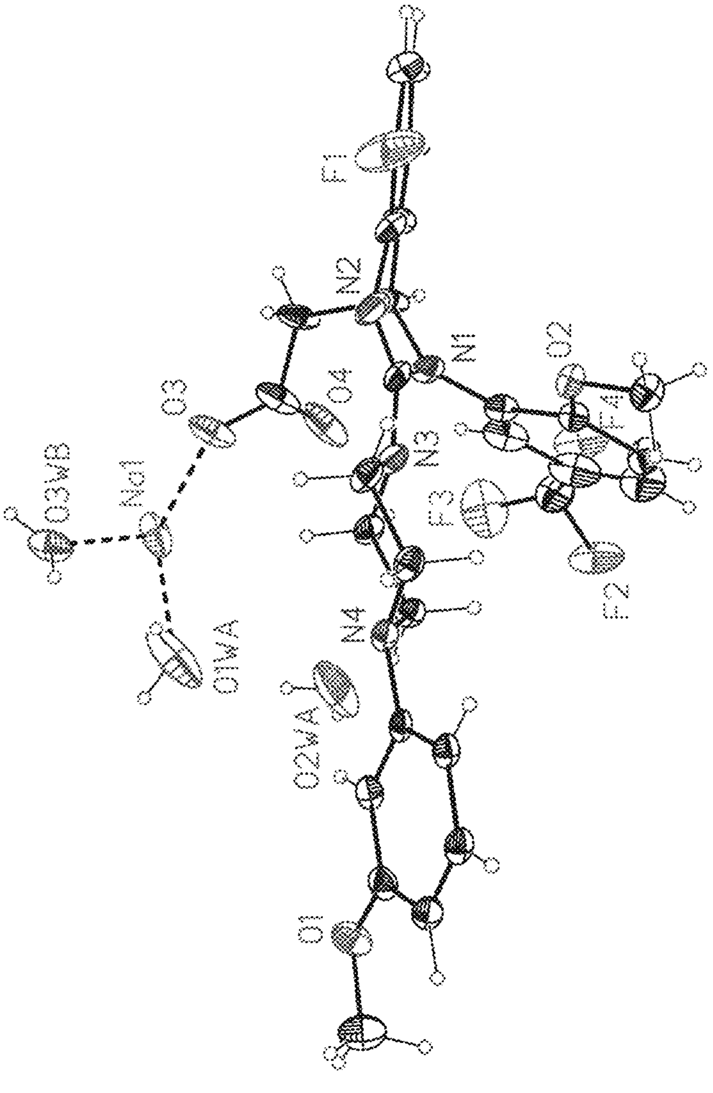
FIG. 5 shows the crystal structure of letermovir sodium trihydrate. Thermal ellipsoids are shown with an electron density set at 50% probability level.
Figure 6:
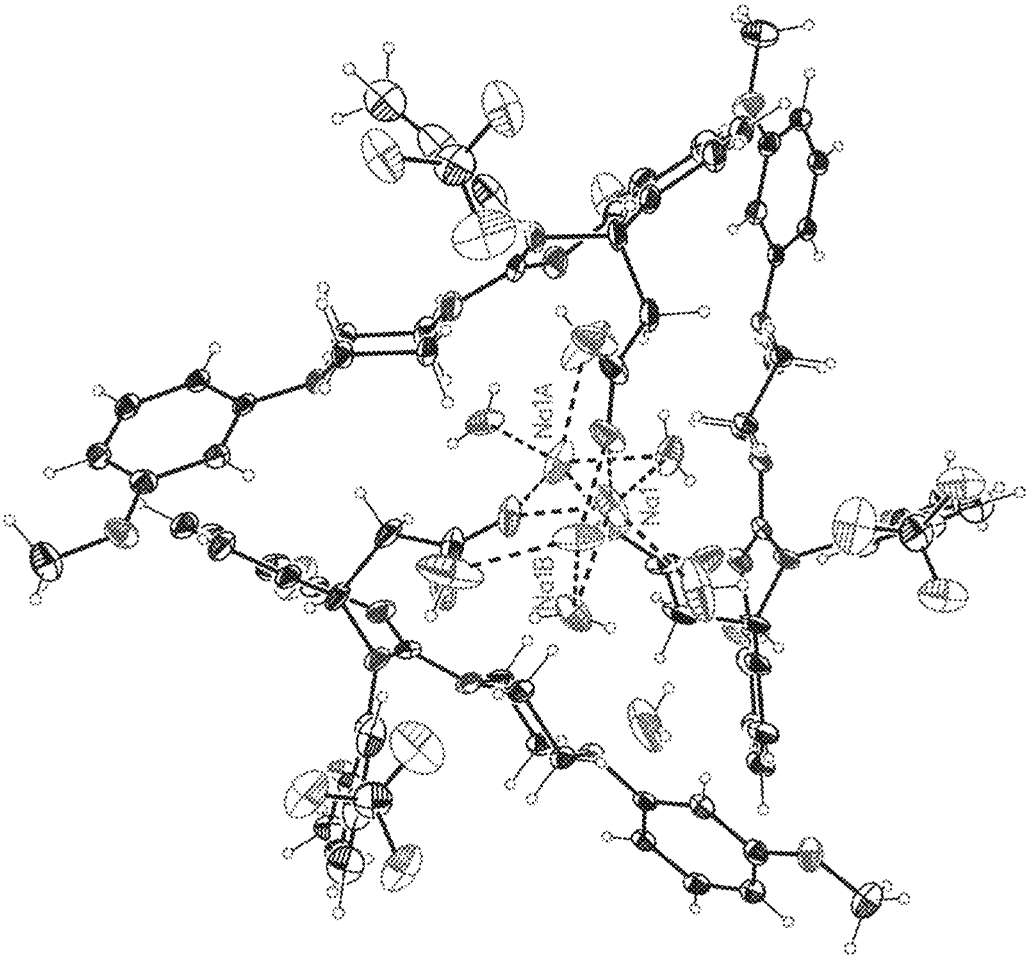
FIG. 6 shows the trimeric complex formed by three Letermovir anions.

The asymmetric unit contains one molecule of Letermovir in anionic form, a sodium cation and three molecules of water. The content of the asymmetric unit is represented in FIG. 5 (disordered atoms have been avoided). The water molecules are each disordered in two positions with ratios of 77:23, 67:33 and 63:37. The CF3-group is also disordered in two orientations with a ratio of 63:37. The trihydrate crystallizes in the highly symmetrical trigonal space group R3 forming a trimeric complex in which three Letermovir anions are forming a channel where the sodium cations and the water molecules are contained (FIG. 6). The carboxylates with the negative charge are inside the channel interacting with the sodium cations.

TABLE 6

| Crystal data | | |
|---|---|---|
| Identification code | mo_P0821002_0m | |
| Empirical formula | $C_{29}H_{27}F_4N_4Na_1O_4$ •3 × $H_2O$ | |
| Formula weight | 648.58 | |
| Temperature | 100(2) K | |
| Wavelength | 0.71073 Å | |
| Crystal system | Trigonal | |
| Space group | R3:H | |
| Unit cell dimensions | a = 28.2198(15) Å | □ = 90° |
| | b = 28.2198(15) Å | □ = 90° |
| | c = 9.9699(6) Å | □ = 120° |
| Volume | 6875.9(8) $Å^3$ | |
| Z | 9 | |
| Density (calculated) | 1.410 $mg/m^3$ | |
| Absorption coefficient | 0.115 $mm^{-1}$ | |
| F(000) | 3042 | |
| Crystal size | 0.50 × 0.40 × 0.20 mm3 | |
| Theta range for data collection | 2.206 to 32.514° | |
| Index ranges | $-42 \leq h \leq 40$, $-40 \leq k \leq 42$, $-9 \leq l \leq 14$ | |
| Reflections collected | 44772 | |
| Independent reflections | 8331[R(int) = 0.0255] | |
| Completeness to theta = 32.514° | 95.50% | |
| Absorption correction | Multi-scan | |
| Max. and min. transmission | 0.74 and 0.69 | |
| Refinement method | Full-matrix least-squares on $F^2$ | |
| Data/restraints/parameters | 8331/231/511 | |
| Goodness-of-fit on F2 | 1.044 | |
| Final R indices [I > 2sigma(I)] | $R_1$ = 0.0460, $wR_2$ = 0.1083 | |
| R indices (all data) | $R_1$ = 0.0483, $wR_2$ = 0.1102 | |
| Flack parameter | x = 0.05(7) | |
| Largest diff. peak and hole | 0.563 and −0.589 e · $Å^{-3}$ | |

The invention claimed is:

1. A method of producing a crystalline form of sodium 2-[(4S)-8-fluoro-2-[4-(3-methoxyphenyl)piperazin-1-yl]-3-[2-methoxy-5-(trifluoromethyl)phenyl]-4H-quinazolin-yl] acetate trihydrate of formula (I)

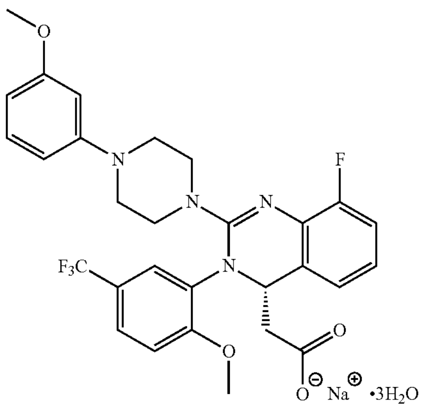 [SMILES: COc1cccc(N2CCN(C3=Nc4c(F)cccc4[C@H](CC(=O)[O-])N3c3cc(C(F)(F)F)ccc3OC)CC2)c1 ; [Na+]]

the method comprising the steps:

Step 1) providing a solution of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid in a mixture of a ($C_1$-$C_6$) alkyl acetate and a ($C_1$-$C_6$) dialkyl ether, wherein the molar ratio of ($C_1$-$C_6$) alkyl acetate:($C_1$-$C_6$) dialkyl ether is from 1:1 to 1:3 in a concentration range of from 0.3 M to 0.7 M;

Step 2) adding 1.0 to 2.0 mole equivalents of an aqueous sodium hydroxide solution based on the 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid content to the solution resulting from step 1 to provide a mixture;

Step 3) stirring the mixture resulting from step 2 for at least 30 minutes at a temperature in the range of from 30° C. to 60° C. to obtain a suspension containing a solid compound;

Step 4) separating the solid compound from the suspension resulting from step 3; and Step 5) drying the solid compound resulting from step 4 at a temperature in the range of from 30° C. to 60° C. for at least one hour to obtain crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate.

2. The method according to claim 1, wherein the concentration of sodium hydroxide in the aqueous sodium hydroxide solution of step 2 is in the range of from 5 M to 30 M.

3. The method according to claim 1, wherein 1.1 to 1.5 mole equivalents of sodium hydroxide based on the 2-[(4S)-8-fluoro-2-[4-(3-methoxyphenyl)-piperazin-1-yl]-3-[2-methoxy-5-(trifluoromethyl)phenyl]-4H-quinazolin-4-yl] acetic acid content are added in step 2 as an aqueous solution at a concentration of sodium hydroxide in the range of from 10 M to 30 M.

4. The method according to claim 1, wherein step 3 further comprises:

cooling down the stirred suspension to room temperature at a cooling rate of 60 K per hour or below, filtering the cooled suspension to provide a solid compound, and optionally washing the solid compound with the ($C_1$-$C_6$) dialkyl ether, which is the ($C_1$-$C_6$) dialkyl ether used in step 1.

5. The method according to claim 1, wherein the ($C_1$-$C_6$) alkyl acetate is methyl acetate, propyl acetate, isopropyl acetate or butyl acetate, or a mixture thereof and the ($C_1$-$C_6$) dialkyl ether is diisopropyl ether, methoxypentane, or methyl tert-butyl ether, or a mixture thereof.

6. The method according to claim 1, wherein in step 1 the concentration of the solution of 2-[(4S)-8-fluoro-2-[4-(3-methoxyphenyl)-piperazin-1-yl]-3-[2-methoxy-5-(trifluoromethyl)phenyl]-4H-quinazolin-4-yl]acetic acid is between 0.3 M to 0.6 M.

7. The method according to claim 1, wherein in step 5, drying the solid compound is performed at a pressure below 10 hPa.

8. The method according to claim 1, wherein step 2 further comprises:

inoculating the solution with seed crystals of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate in an amount of from 0.5 to 1 wt % based on the total weight of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid provided in step 1.

9. A method comprising:

producing a crystalline form of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate of formula (I) according to the method of claim 1, and micronizing or nanomiling the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate resulting from step 5 to obtain a pharmaceutical composition comprising the micronized crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate, wherein the particle size is in a range of 0.3 to 1000 μm and the particle size distribution is defined by d(0.1) from 1 to 100 μm, d(0.5) from 30 to 250 μm and d(0.9) from 100 to 800 μm.

10. A method comprising:

producing a crystalline form of sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate of formula (I) according to the method of claim 1, and adding at least one pharmaceutically acceptable carrier, excipient and/or diluent to the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate.

11. A crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate of formula (I)

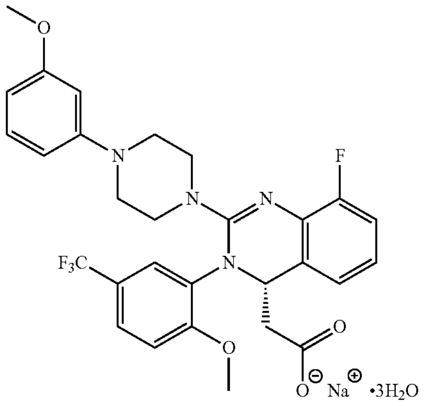 [SMILES: COc1cccc(N2CCN(C3=Nc4c(F)cccc4[C@H](CC(=O)[O-])N3c3cc(C(F)(F)F)ccc3OC)CC2)c1 ; [Na+]]

having a hexagonal crystal system, a space group of R3, and a unit cell dimension of a=28.22 Å, b=28.22 Å, c=9.97 Å, α=90±3°, β=90±3°, and γ=120±3° which is obtainable by the method as defined in claim 1.

12. The crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate according to claim 11 which is essentially free from ethanol.

13. A crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate having a trigonal crystal system, a space group of R3, and a unit cell dimension of a=28.22 Å, b=28.22 Å, c=9.97 Å, α=90±3°, β=90±3°, and γ=120±3°.

14. The crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate according to claim 11, wherein the X-ray diffraction pattern of said crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate comprises 2-theta angle values of 6.2, 9.5, 12.4, 15.6, 18.0, 19.0, 21.0, 22.5 and 26.8 degrees, and said 2-theta angle values have a normal deviation of ±0.1°.

15. A pharmaceutical composition comprising the crystalline sodium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate trihydrate as defined in claim 11, and at least one pharmaceutically acceptable carrier, excipient and/or diluent.

16. The pharmaceutical composition according to claim 15 which is a dry powder.

17. The pharmaceutical composition according to claim 15, which is essentially free from ethanol.

18. The pharmaceutical composition according to claim 15 that is suitable for intravenous administration.

19. The pharmaceutical composition according to claim 15 that is suitable for oral administration.

20. The pharmaceutical composition according to claim 15 for use in a method of treatment and/or prevention of virus infections by members of the herpes viridae group.

21. A method for the treatment of a virus infection by a member of the herpes viridae group, comprising administering to an infected subject an effective amount of a pharmaceutical composition according to claim 15.

22. The method according to claim 21, wherein the infected subject is a non-human mammal.

23. The method according to claim 1, wherein in step 1 the temperature of the solution is in the range of from 30° C. to 60° C.

24. The method according to claim 1, wherein the concentration of sodium hydroxide in the aqueous sodium hydroxide solution of step 2 is in the range of from 10 M to 30 M.

25. The method according to claim 1, wherein the ($C_1$-$C_6$) alkyl acetate is isopropyl acetate and the ($C_1$-$C_6$) dialkyl ether is diisopropyl ether.

26. The method according to claim 25, wherein the molar ratio of isopropyl acetate:dialkyl ether is 1:2.

27. The method according to claim 1, wherein in step 5, drying the solid compound is performed at a pressure of 2 to 3 hPa at 50° C. for 15 hours.

28. A method for the treatment of a human cytomegalovirus (HCMV) infection comprising administering to an infected subject an effective amount of a pharmaceutical composition according to claim 15.

29. The method according to claim 21, wherein the infected subject is a human.

* * * * *